United States Patent [19]

Mandon et al.

[11] Patent Number: 4,630,775

[45] Date of Patent: Dec. 23, 1986

[54] DISPENSER FOR RELEASING A VOLATILE ACTIVE SUBSTANCE

[75] Inventors: Jean-Pierre Mandon, Chasseneuil du Poitou; Jean Rapiteau, Saint Benoit, both of France

[73] Assignee: Airwick Industries, Inc., Carlstadt, N.J.

[21] Appl. No.: 730,527

[22] Filed: May 6, 1985

[30] Foreign Application Priority Data

May 11, 1984 [CH] Switzerland ............ 2334/84

[51] Int. Cl.$^4$ ................................. A61L 9/04
[52] U.S. Cl. ........................ 239/56; 239/59; 206/603
[58] Field of Search ............ 239/34, 37, 42, 57, 239/58, 59, 309, 47, 51.5, 54–56; 222/80, 81, 83, 83.5, 5, 85; 206/5, 603

[56] References Cited

U.S. PATENT DOCUMENTS 3,727,840 4/1973 Nigro ........................... 239/43
4,161,284 7/1979 Retton .......................... 239/43
4,247,042 1/1981 Shimonski ..................... 239/43
4,526,320 7/1985 von Phillip et al. .......... 239/58 X Primary Examiner—Joseph F. Peters, Jr.
Assistant Examiner—Kevin Patrick Weldon
Attorney, Agent, or Firm—Felfe & Lynch

[57] ABSTRACT

A dispenser for releasing a volatile active substance from a carrier material that contains the active substance in liquid form in a receptacle is impermeable to liquid, said dispenser comprising a base circular part with supporting members for said carrier and sidewall sections on which an upper circular part with cylindrical sidewall, pierced by side apertures for the emission of the volatile active substance, is pivoted. The upper circular part has on the inner disc-shaped surface thereof one or more decentrally positioned flexible blades which are able to pierce the sheath of the receptacle containing the active substance or to impale it on a spike by rotating the circular parts relative to each other in order to activate the carrier material by impregnating it with volatile active substance.

6 Claims, 16 Drawing Figures

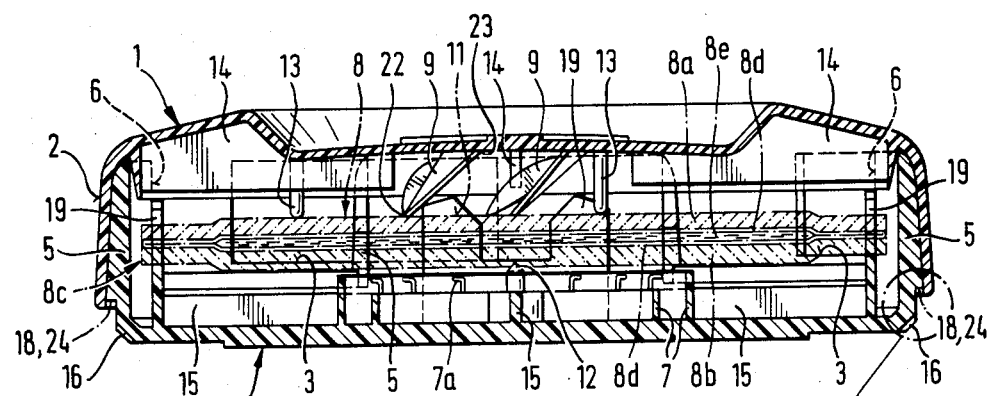
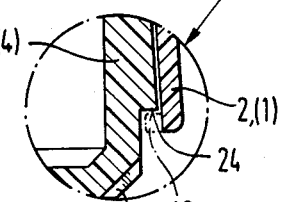
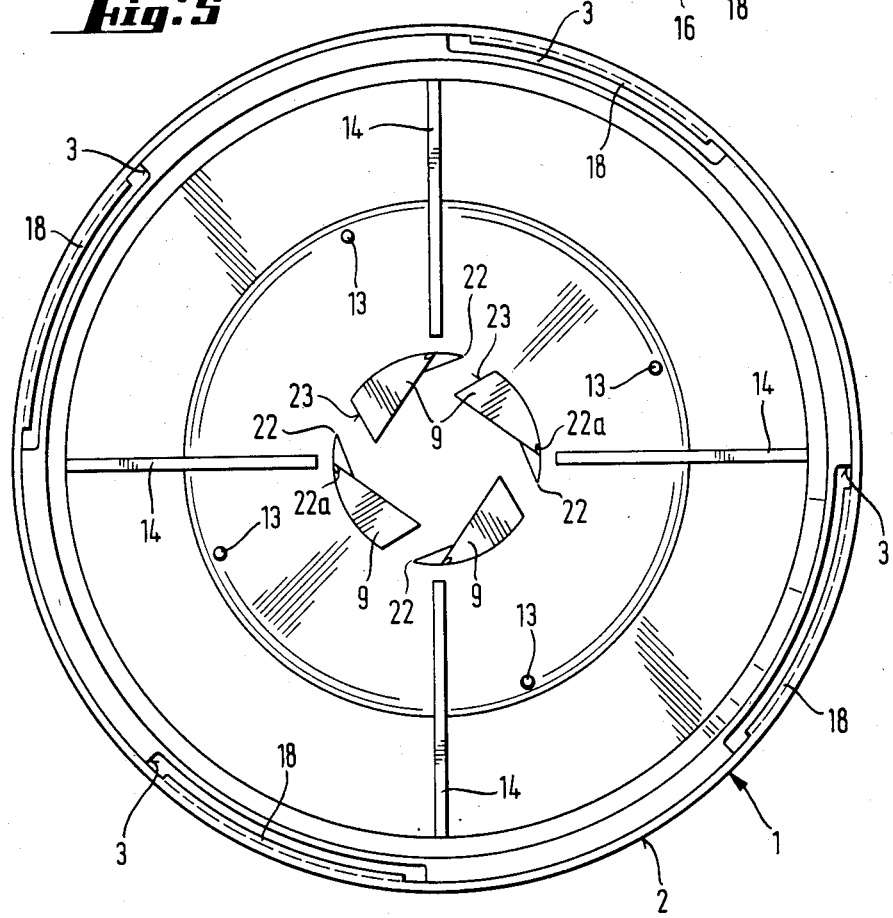

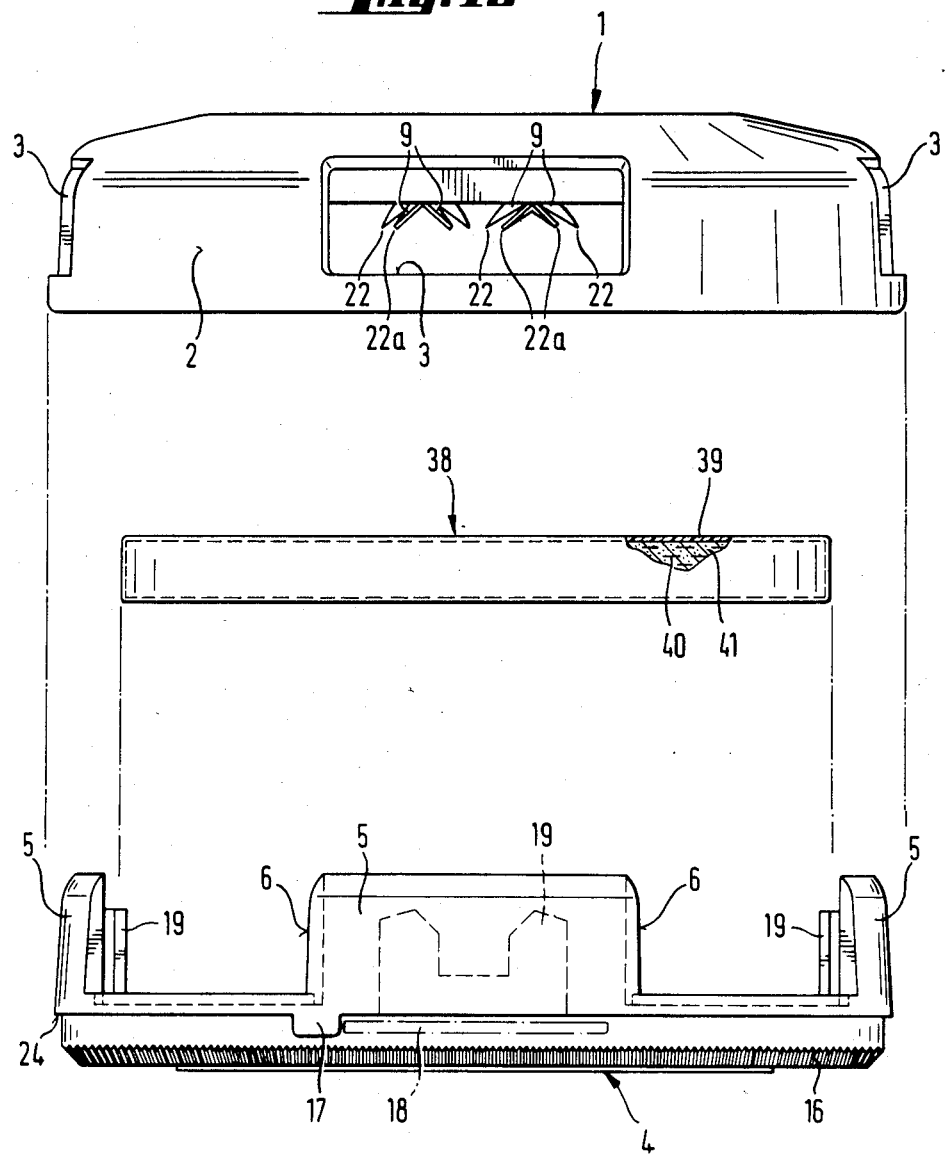

DISPENSER FOR RELEASING A VOLATILE ACTIVE SUBSTANCE

The present invention relates to a dispenser for releasing a volatile active substance, for example for treating the air or for bactericidal or insecticidal purposes.

Many of the hitherto known dispensers for volatile air treating materials employ a carrier material made of an absorbent or porous material which is impregnated with the volatile active substance. The disadvantage of such dispensers is that, depending on the length of time they have previously been stored by the manufacturer or retailer, a substantial amount of the active substance has already been volatilised before first time use.

French patent specification No. 1 231 135 discloses a dispenser for volatile substances consisting of a porous carrier that contains a liquid active substance in a sachet which is impermeable to liquid and is masked by a strip of metal foil. By exerting pressure on the metal foil, the sachet is squashed or perforated by pointed or angular pieces of metal positioned between the sachet and the carrier material, so that the active substance flows out of the sachet and is absorbed by the porous carrier material for gradual release into the ambient air. The shortcoming of this dispenser is that the release of the volatile active substance cannot be controlled.

Accordingly, it is the object of the present invention to provide a dispenser that is able to prevent the premature volatilisation of the active substance as well as to control the release of volatile active substance to the ambient air whenever required.

This object is achieved by means of the dispenser of this invention for releasing a volatile active substance from a carrier material that contains the active substance in liquid form in a receptacle that is impermeable to liquid, said dispenser comprising a base circular part 4 with supporting members for said carrier and sidewall sections on which another (upper) circular part 1 with cylindrical sidewall 2, pierced by side apertures 3 for the emission of the volatile active substance, is pivoted, said upper circular part 1 having on the inner disc-shaped surface thereof one or more decentrally positioned flexible blades 9 which are able to pierce the sheath of the receptacle containing the active substance or to impale it on spike 12 by rotating parts 1 and 4 counterclockwise relative to each other in order to activate the carrier material by impregnating it with volatile active substance.

Preferably the flexible blades are inclined with respect to the direction of rotation of upper circular part 1 relative to base circular part 4 at the inner disc-shaped surface of upper circular part 1. The flexible blades can have cutting edges or barbs at their outer end, the tips of which are held fast in the carrier material during the first counterclockwise rotation of both circular parts 1 and 4 are pierce or impale the sheath of the receptacle containing the active substance in order to rupture it. The cutting edges can be provided with a prong at their extremity for better retention in the carrier.

A dispenser of the kind discussed above is illustrated by the following FIGS. 1 to 9:

Figure 1:
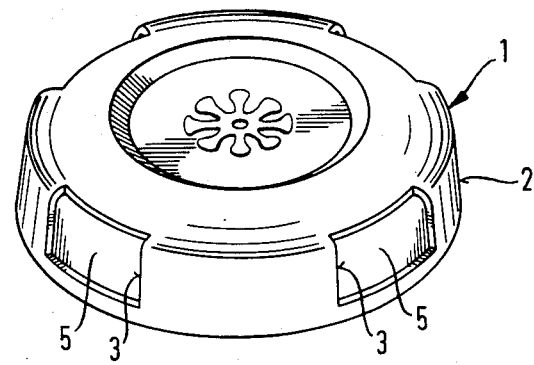
FIG. 1 is a perspective drawing with closed side apertures.
Figure 2:
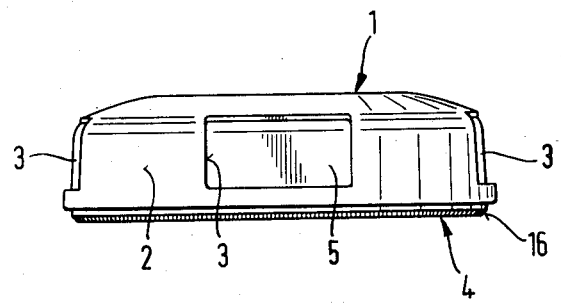
FIG. 2 shows a side view of the dispenser, also with closed apertures.
Figure 3:
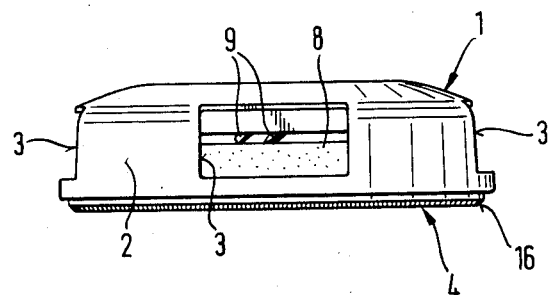
FIG. 3 shows a side view of the open dispenser.

FIGS. 4 to 9 reproduce the dispenser enlarged to approximately twice the size compared with FIGS. 1 to 3.

FIG. 4 illustrates a vertical section through the entire dispenser with not yet activated carrier material.

FIG. 5 is a view of the inner disc-shaped surface of the part with the side apertures and for decentrally positioned ploughshare-shaped flexible blades.

Figure 6:
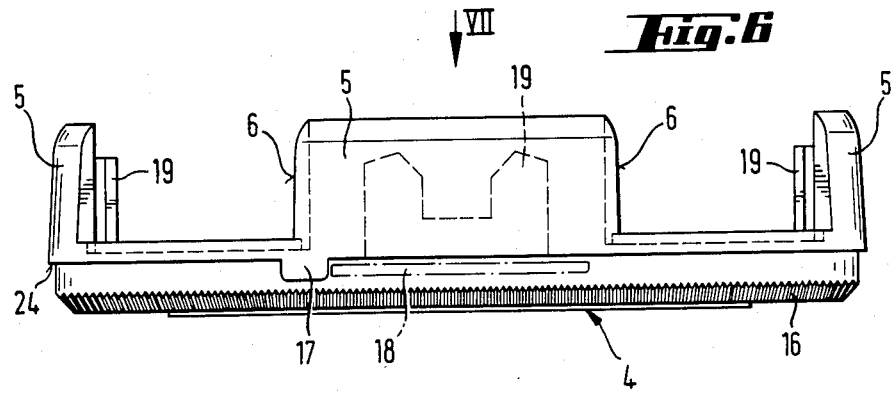

FIG. 6 is a side view of the circular part with the sidewall sections.

Figure 7:
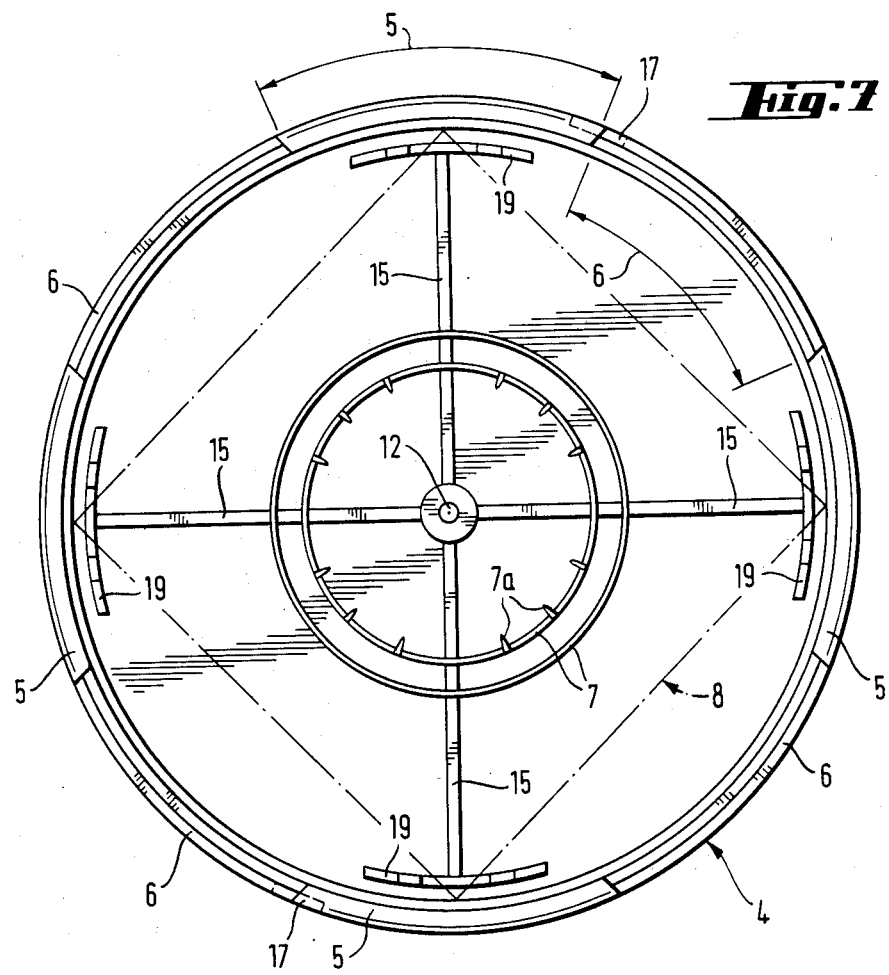

FIG. 7 is a view of the inner disc-shaped surface of the circular part in the direction VII of FIG. 6 with dotted outline of the carrier material.

Figure 8:
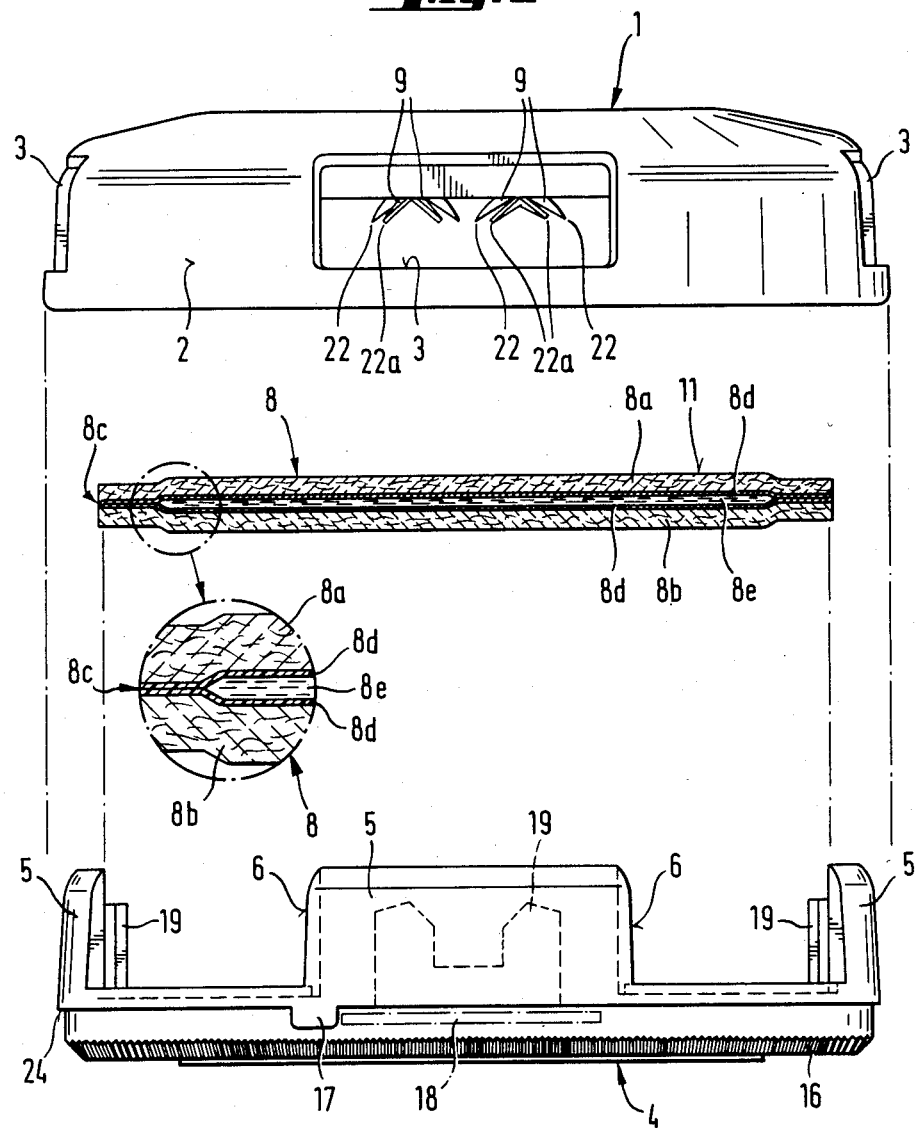
Figure 9:
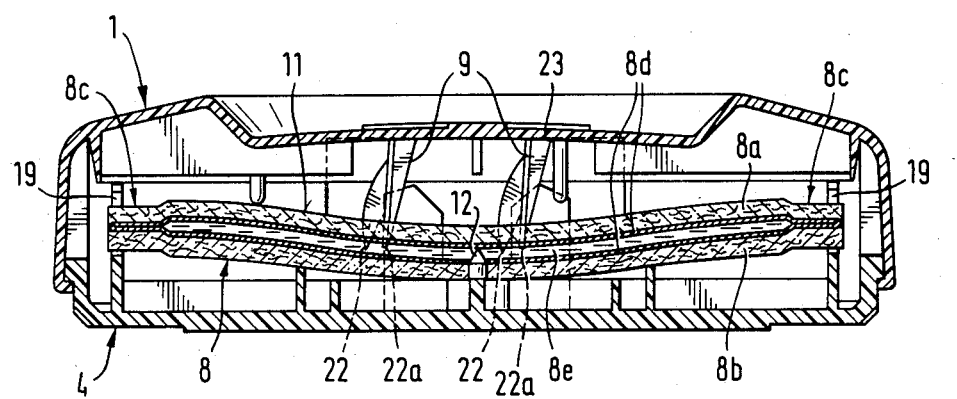

FIG. 8 is a side view of all parts as explosion drawing, and FIG. 9 is a vertical section corresponding to FIG. 4, but with activated carrier.

FIG. 10 is an exploded view of an alternate embodiment of this invention.

Individually, FIGS. 1 to 9 show that the dispenser for releasing a volatile active substance comprises two reciprocally rotating and engaging circular parts 1 and 4 and the carrier material 8. Upper circular part 1 has a plurality of apertures 3 at the annular sidewall 2 thereof, which apertures may be partly or completely covered by the sidewall sections 5 of base circular part 4. The reciprocal rotatability of circular parts 1 and 4 also effects a continuous adjustment of the size of the apertures 3. Between the individual sidewall sections 5 of base circular part 4 are apertures 6, the areas of 5 and 6 each being more or less equal, as FIG. 7 shows. This ensures that as large a clearance as possible between the two parts of the casing—and thus as great a ventilation as possible—is attained.

As FIGS. 4 and 7 in particular show, there are provided on the inner disc-shaped surface of the base circular part 4 support means 7 and 12 for the carrier material 8 which contains the active substance in a receptacle which is impermeable to liquid and which surrounds it in compact form. When it is square-shaped, the support 8 which rests on the support members 7 and 12 is secured against lateral displacements with the corners thereof in the notches of the guide ribs 19, which are parallel to the sidewall sections 5 on the inner disc-shaped surface of the base circular part 4. As illustrated in FIG. 4, the carrier material 8 is held down on the support members 7 and 12 by the vertical pins 13 in upper circular part 1.

In FIGS. 4, 5 and 9, the decentrally positioned flexible blades 9 can be seen on the inner disc-shaped surface of upper circular part 1. They are attached by hinges 23 flexibly to the inside of upper circular part 1 and are preferably made, in a single casting, with upper circular part 1 from thermoplastic material. In the illustrated inclined form of the blades 9, these are provided at the outer end with cutting edges 22, each of which may have a prong 22a at the extremity, which prong is held fast in the outer layer 11 of the carrier material 8, 8a when upper circular part 1 in part 4 is rotated counterclockwise. As a consequence of being held fast, the blades 9 bend against the rotation, thereby causing the cutting edges 22 at the end of the blades 9 to penetrate the carrier material and to rupture the sheath of the receptacle 8d which is impermeable to liquid. The liquid active substance 8e then flows out of the receptacle 8d and impregnates the carrier material 8, 8a, 8b from which said active substance can be released into the ambient air, in volatile form, through the side apertures 3. The carrier material 8 may suitably be paper, cardboard, fibrous or sponge-like material made of plastic or the like, which material can be impregnated with liquid active substances or solvents that contain active substances. The carrier material is preferably formed of two layers 8*a* and 8*b* and, through weld joints 8*c*, comprises a double-layered receptacle 8*d* which is impermeable to liquid and made of sheet material and which is filled with liquid active substance 8*e* (FIG. 8).

Circular parts 1 and 4 will normally be made in one piece from moulded plastics material. Although these parts will preferably be made from polyethylene, polypropylene or polyvinyl chloride, it will be understood that other kinds of plastics materials can also be used and that both parts can be formed from the same or different plastics materials.

The dispenser illustrated in FIGS. 1 to 9 represents only one of many possible embodiments. The outer form of said dispenser is already the subject matter of various patent and trademark rights, for example Spanish Utility Model No. 261 291. Essentially, it shall be shown how the decentral assembly of flexible blades for rupturing the sheath of the receptacle containing the active substance in the carrier material, and so activating said carrier material by impregnating it just before first time use, may appear. The form of the blades may also vary, their sole purpose being to activate the carrier material on opening the side apertures for the first time in order to prevent premature loss of active substance through volatilisation.

Further parts in the figures can be, for example, stiffening ribs 14 and 15 in circular parts 1 and 4, a serration 16 in base circular part 4 which facilitates opening and closing of the dispenser, buffers 17 in base circular part 4 and projections 18 in upper circular part 1 which restrict the path of rotation of circular parts 1 and 4 relative to each other, for which purpose the shoulder joint 24 also serves. Finally, the centrally positioned spike 12 can also act as fixing member instead of supporting member in that the extended upper part thereof protrudes through a central aperture which is impermeable to liquid present in the carrier material, the receptacle which contains the active substance having the form of a ring or the like around the aperture. Additional fixation of the carrier material can be effected by means of short teeth 7*a* in the supporting ring 7, as shown in FIG. 7.

Where there is no central aperture in the carrier material, the spike 12 can also act as means for rupturing the sheath of the receptacle containing the active substance. In this case, for example, activation is effected by flexible blades 9 exerting downwards pressure on the carrier material, which is then pressed onto the spike 12, which pierces the receptacle 8*d* (FIG. 9).

FIG. 10 illustrates another form of receptacle 38 that contains active substance and which can be employed with the dispenser as shown in FIGS. 1 to 9. Here the carrier material 41 is already impregnated with active substance 40. The cutting edges of the blades 9 rupture the envelope 39 which is impermeable to active substance such that rents are made through which the active substance is able to be volatilised.

The dispenser is intended for the controlled release of volatilised amounts of liquid active substance contained in a carrier material. The spatial distribution of an air treating material is the particularly preferred utility. However, it is also possible to release other volatile active substances, for example insecticides or bactericides, into the ambient atmosphere in similar manner.

What is claimed is:

1. A dispenser for releasing a volatile active substance from a carrier material which surrounds a liquid-impermeable sheath containing the active substance in liquid form, said dispenser comprising:

a base circular part having supporting members for said carrier material and having a sidewall section with a plurality of apertures;

an upper circular part rotatably mounted on the base circular part and having a cylindrical sidewall section with a plurality of apertures equal in number and size to the apertures on the sidewall section of said base circular part, the upper circular part adapted to be rotated relative to the base circular part so as to cause the respective apertures to be in an open position in register with each other, in a partially open position in partial register with each other, or in a closed position out of register with each other; and at least one decentrally positioned flexible blade disposed on the inner surface of said upper circular part and adapted, upon rotation of the upper circular part from the closed position to a partially open position, to pierce the sheath containing said active substance, thereby causing the carrier material to be impregnated with the active substance.

2. A dispenser according to claim 1 wherein the flexible blades are inclined with respect to the axis of rotation of the upper circular part relative to the base circular part at the inner surface of said upper circular part.

3. A dispenser according to claim 2 wherein the flexible blades are provided with cutting edges at their outer ends.

4. A dispenser according to claim 3 wherein each cutting edge is provided with a prong at its extremity.

5. A dispenser according to claim 1 wherein the base circular part is provided with a spike at its centre which provides additional support for the carrier material and which is adapted, upon rotation of the upper circular part from the closed position to a partially open position to pierce the sheath containing the active substance.

6. A dispenser for releasing a volatile active substance from a carrier material impregnated therewith and surrounded by an impermeable envelope, said dispenser comprising:

a base circular part having supporting members for said carrier material and having a sidewall section with a plurality of apertures;

an upper circular part rotatably mounted on the base circular part and having a cylindrical sidewall section with a plurality of apertures equal in number and size to the apertures on the sidewall section of said base circular part, the upper circular part adapted to be rotated relative to the base circular part so as to cause the respective apertures to be in an open position in register with each other, in a partially open position in partial register with each other, or in a closed position out of register with each other; and at least one decentrally positioned flexible blade disposed on the inner surface of said upper circular part and adapted, upon rotation of the upper circular part from the closed position to a partially open position, to pierce the envelope containing the impregnated carrier material.

* * * * *